US011083607B2

(12) United States Patent
Paquin et al.

(10) Patent No.: US 11,083,607 B2
(45) Date of Patent: Aug. 10, 2021

(54) DELIVERY BALLOON WITH RETRACTABLE RETENTION CUFFS

(71) Applicant: Zorion Medical, Inc., Zionsville, IN (US)

(72) Inventors: Mark Paquin, Indianapolis, IN (US); David Broecker, Zionsville, IN (US)

(73) Assignee: Zorion Medical, Inc., Zionsville, IN (US)

( * ) Notice: Subject to any disclaimer, the term of this patent is extended or adjusted under 35 U.S.C. 154(b) by 178 days.

(21) Appl. No.: 16/151,930

(22) Filed: Oct. 4, 2018

(65) Prior Publication Data
US 2019/0201224 A1  Jul. 4, 2019

Related U.S. Application Data

(60) Provisional application No. 62/568,123, filed on Oct. 4, 2017.

(51) Int. Cl.
*A61F 2/958* (2013.01)

(52) U.S. Cl.
CPC ...... *A61F 2/958* (2013.01); *A61F 2002/9583* (2013.01); *A61F 2002/9586* (2013.01); *A61F 2210/0004* (2013.01); *A61F 2230/0067* (2013.01); *A61F 2250/0039* (2013.01)

(58) Field of Classification Search
CPC .............. A61F 2/958; A61F 2250/0039; A61F 2002/9583; A61F 2230/0067; A61F 2210/0004; A61F 2002/9586
See application file for complete search history.

(56) References Cited

U.S. PATENT DOCUMENTS

| | | | | |
|---|---|---|---|---|
| 6,174,316 | B1 * | 1/2001 | Tuckey | A61F 2/958 606/108 |
| 6,280,412 | B1 * | 8/2001 | Pederson, Jr. | A61F 2/958 604/103.07 |
| 6,387,118 | B1 | 5/2002 | Hanson | |
| 6,562,061 | B1 | 5/2003 | Wang et al. | |
| 6,565,595 | B1 * | 5/2003 | DiCaprio | A61F 2/958 623/1.11 |
| 6,699,273 | B2 * | 3/2004 | Langan | A61M 25/10 604/103 |

(Continued)

OTHER PUBLICATIONS

International Search Report and Written Opinion of the International Searching Authority from corresponding PCT Application No. PCT/US2018/054382, dated Jan. 17, 2019 (11 pages).

*Primary Examiner* — Anh T Dang
(74) *Attorney, Agent, or Firm* — Quarles & Brady LLP

(57) ABSTRACT

A balloon system for delivery of a device. The balloon system includes a balloon including: an elongated central portion including a proximal tapered cone and a distal tapered cone, the elongated central portion and the proximal and distal tapered cones being in an uninflated state; a proximal receiving trench adjacent the proximal tapered cone and a distal receiving trench adjacent the distal tapered cone, and a distal backstop adjacent the distal receiving trench, the distal receiving trench being defined by the distal backstop and the distal tapered cone; and a proximal retractable cuff disposed over the proximal receiving trench and the proximal tapered cone and a distal retractable cuff disposed over the distal receiving trench and the distal tapered cone.

32 Claims, 11 Drawing Sheets

(56) References Cited

U.S. PATENT DOCUMENTS

| | | |
|---|---|---|
| 9,061,126 B2 | 6/2015 | Fischell et al. |
| 2001/0027337 A1* | 10/2001 | Di Caprio ............... A61F 2/958 |
| | | 623/1.11 |
| 2002/0138128 A1* | 9/2002 | Stiger .................... A61F 2/958 |
| | | 623/1.11 |
| 2003/0033000 A1 | 2/2003 | DiCaprio et al. |
| 2003/0060832 A1* | 3/2003 | Guinan .................. A61F 2/958 |
| | | 606/108 |
| 2003/0074044 A1 | 4/2003 | Randby et al. |
| 2009/0281617 A1 | 11/2009 | Cottone et al. |
| 2013/0253466 A1* | 9/2013 | Campbell ......... A61M 25/1029 |
| | | 604/500 |

* cited by examiner

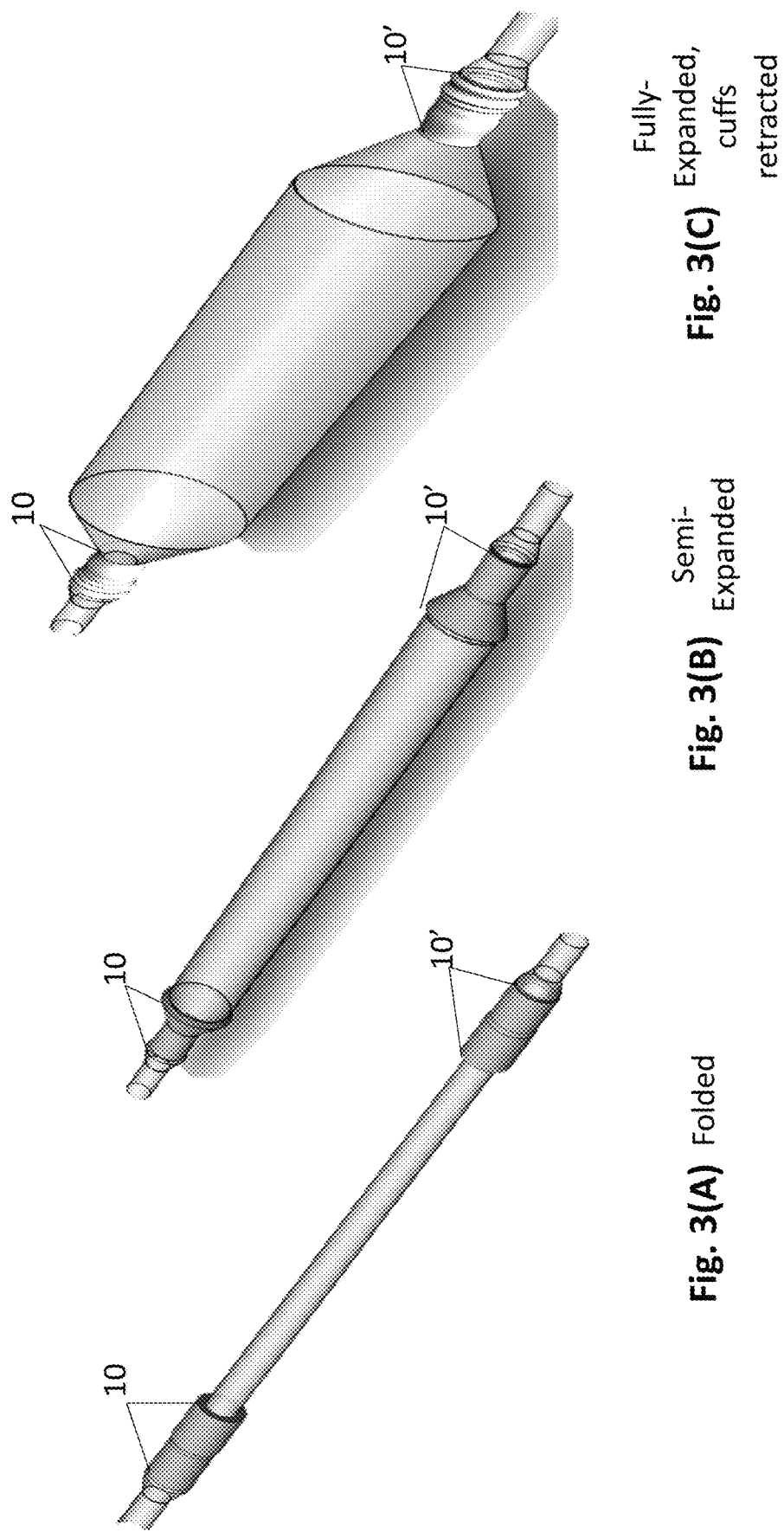

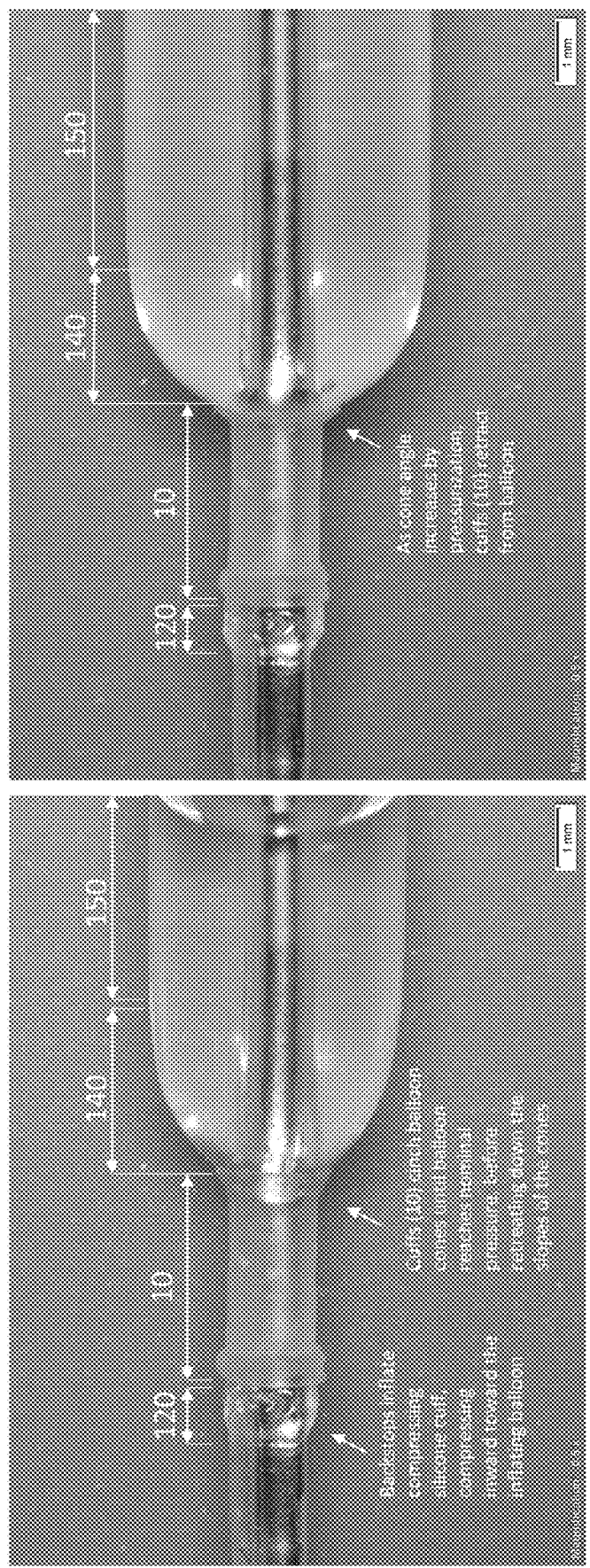

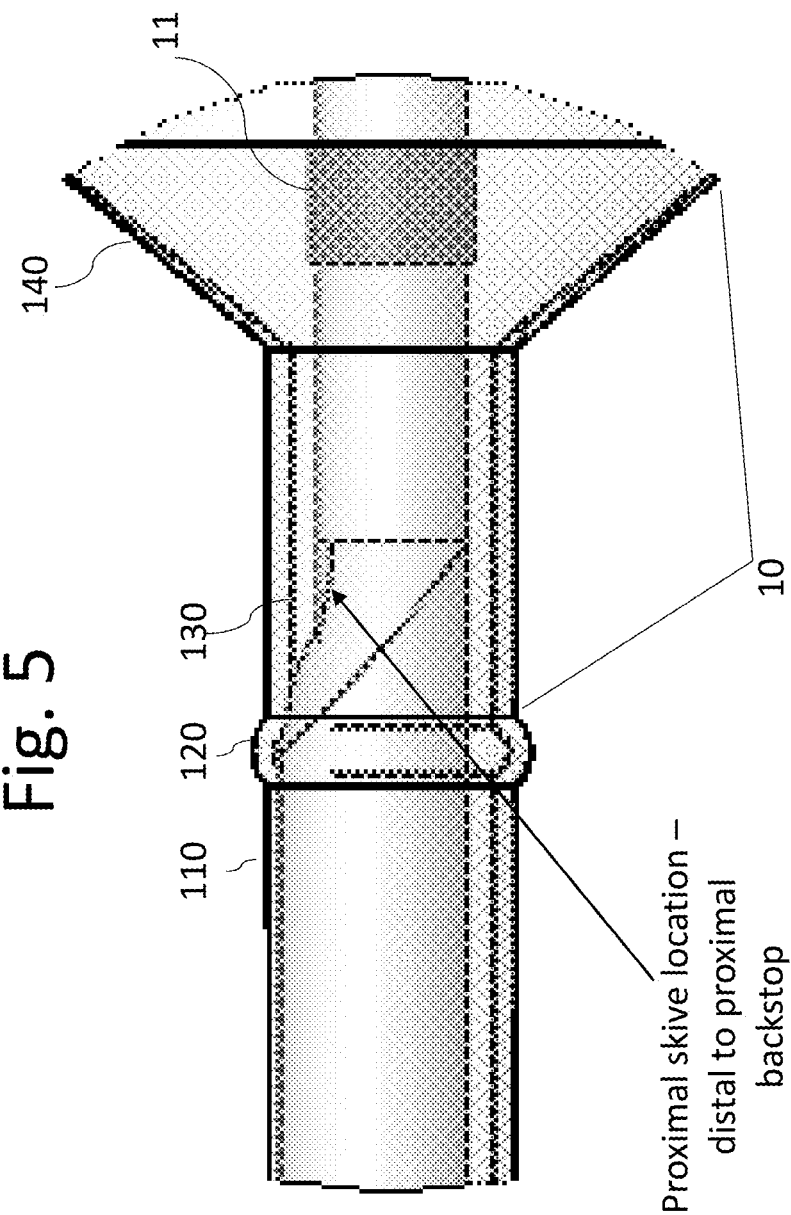

DELIVERY BALLOON WITH RETRACTABLE RETENTION CUFFS

CROSS-REFERENCE TO RELATED APPLICATIONS

This application is based on, and claims the benefit of, U.S. Provisional Patent Application No. 62/568,123, filed Oct. 4, 2017, which is hereby incorporated herein by reference in its entirety for all purposes.

FIELD OF THE INVENTION

This document concerns an invention relating generally to a balloon that is adapted for placing stents, for example bioabsorbable vascular stents/scaffolds, into vessels.

BACKGROUND OF THE INVENTION

Stents are used throughout the body, although in general they have been used with much greater frequency in arteries than in other structures of the body. Bare stents were introduced in the 1990's, followed by introduction of drug-eluting stents (DES) in the early 2000's.

Stenting changed with the introduction of bioabsorbable vascular stents/scaffolds (BVS) in 2012. BVSs are absorbable implants that degrade and metabolize over time. They provide all the same benefits as contemporary DESs with the additional advantage of being non-permanent.

The issue with BVSs, however, remains the ability for a user (e.g. a clinician) to advance, precisely deploy, and expand (and potentially re-expand) the devices safely and effectively. Furthermore, unlike contemporary stents, BVSs are typically made from non-radiopaque materials and as such cannot be visualized using conventional X-ray technologies. As a result, malapposed and floating struts may go unnoticed and may lead to adverse events, such as blood clots.

Unlike permanent stents, BVS are bulkier and more fragile. The bulkiness is associated with the need to make BVS stronger by using larger quantities of biomaterials. Fragility on the other hand, is due to the type(s) and composition of biomaterials used, and how the biomaterials are processed which in turn dictate how strong and ductile the BVS will be. Thus, companies developing BVS technologies have had to not only find innovative ways to ensure safe and reliable deliverability of BVS while being maneuvered through blood vessels, but also have had to develop innovative ways to safely and reliably deploy and expand BVS into blood vessels.

SUMMARY OF INVENTION

Thus, there is a need for improved methods for ensuring safe and reliable deliverability of stents and other balloon-deliverable devices. Although certain examples disclosed herein pertain to BVS stents, the disclosed balloon system is generally applicable for a number of uses and can be used with a variety of stents and other balloon-deliverable devices (e.g. meshes). Devices such as BVSs often require delivery balloons capable of precisely and uniformly expanding a structure without placing undue stress on its material and scaffolding. Accordingly, there is a need to develop innovative ways to safely and reliably deploy, expand, and potentially re-expand BVSs at the treatment site without having to switch out balloons.

In one embodiment the invention is a balloon system for delivery of a device. The balloon system includes a balloon including: an elongated central portion including a proximal tapered cone and a distal tapered cone, the elongated central portion and the proximal and distal tapered cones being in an uninflated state; a proximal receiving trench adjacent the proximal tapered cone and a distal receiving trench adjacent the distal tapered cone, and a distal backstop adjacent the distal receiving trench, the distal receiving trench being defined by the distal backstop and the distal tapered cone; and a proximal retractable cuff disposed over the proximal receiving trench and the proximal tapered cone and a distal retractable cuff disposed over the distal receiving trench and the distal tapered cone.

In another embodiment the invention is a balloon system for delivery of a device. The balloon system includes a balloon including: an elongated central portion including a first tapered cone at a first end thereof and a second tapered cone at a second end thereof, the elongated central portion and the first and second tapered cones being in an uninflated state; a first receiving trench adjacent the first tapered cone and a second receiving trench adjacent the second tapered cone, and a first backstop adjacent the first receiving trench and a second backstop adjacent the second receiving trench, the first receiving trench being defined by the first backstop and the first tapered cone and the second receiving trench being defined by the second backstop and the second tapered cone; and a first retractable cuff disposed over the first receiving trench and the first tapered cone and a second retractable cuff disposed over the second receiving trench and the second tapered cone, upon inflation of the balloon, the first retractable cuff retracting from the first tapered cone such that the first retractable cuff is disposed substantially within the first receiving trench, and the second retractable cuff retracting from the second tapered cone such that the second retractable cuff is disposed substantially within the second receiving trench.

In yet another embodiment the invention is a method of placing a device in a vessel. The method includes steps of: inserting a catheter including a balloon system into the vessel, the balloon system including a balloon, a proximal retractable cuff, and a distal retractable cuff, the balloon including: an elongated central portion including a proximal tapered cone and a distal tapered cone, the elongated central portion and the proximal and distal tapered cones being in an uninflated state, and the device being disposed around the elongated central portion, a proximal receiving trench adjacent the proximal tapered cone and a distal receiving trench adjacent the distal tapered cone, and a distal backstop adjacent the distal receiving trench, the distal receiving trench being defined by the distal backstop and the distal tapered cone, and the proximal retractable cuff being disposed over the proximal receiving trench and the proximal tapered cone and the distal retractable cuff being disposed over the distal receiving trench and the distal tapered cone; inflating the balloon with inflation fluid to expand the elongated central portion of the balloon, the device being expanded in cross-sectional size upon inflation of the balloon, and the proximal retractable cuff being retracted from the proximal tapered cone and the distal retractable cuff being retracted from the distal tapered cone upon inflation of the balloon; and deflating the balloon by removing at least a portion of the inflation fluid.

Further advantages and features of the invention will be apparent from the remainder of this document in conjunction with the associated drawings.

DESCRIPTION OF THE DRAWINGS

FIGS. 3(A)-3(C) show a balloon according to an embodiment of the invention with cuffs at each, where the balloon is shown in the initial folded state with the cuffs disposed over the cones (FIG. 3(A)), in a semi-expanded state with the cuffs still covering the cones (FIG. 3(B)), and in a fully-expanded state in which the cuffs have retraced from the cones (FIG. 3(C)).

FIGS. 4(A) and 4(B) show cuffs in the trench region of an embodiment of a balloon mounted on a catheter, at two different stages of inflation, demonstrating how the cuffs retract from the cones and how the cuff may be compressed against the backstop as the cuff retracts from the cone.

FIG. 5 shows a close-up view of an embodiment of a balloon with a cuff, showing a backstop having a rounded cross-sectional shape.

FIG. 8(A) shows a balloon with cuffs in a non-inflated state (top panel) and an inflated state (bottom panel. FIG. 8(B) shows a balloon without cuffs in a non-inflated state (top panel), a partially inflated state (middle panel), and a fully inflated state (bottom panel).

DETAILED DESCRIPTION OF THE INVENTION

Figure 1:
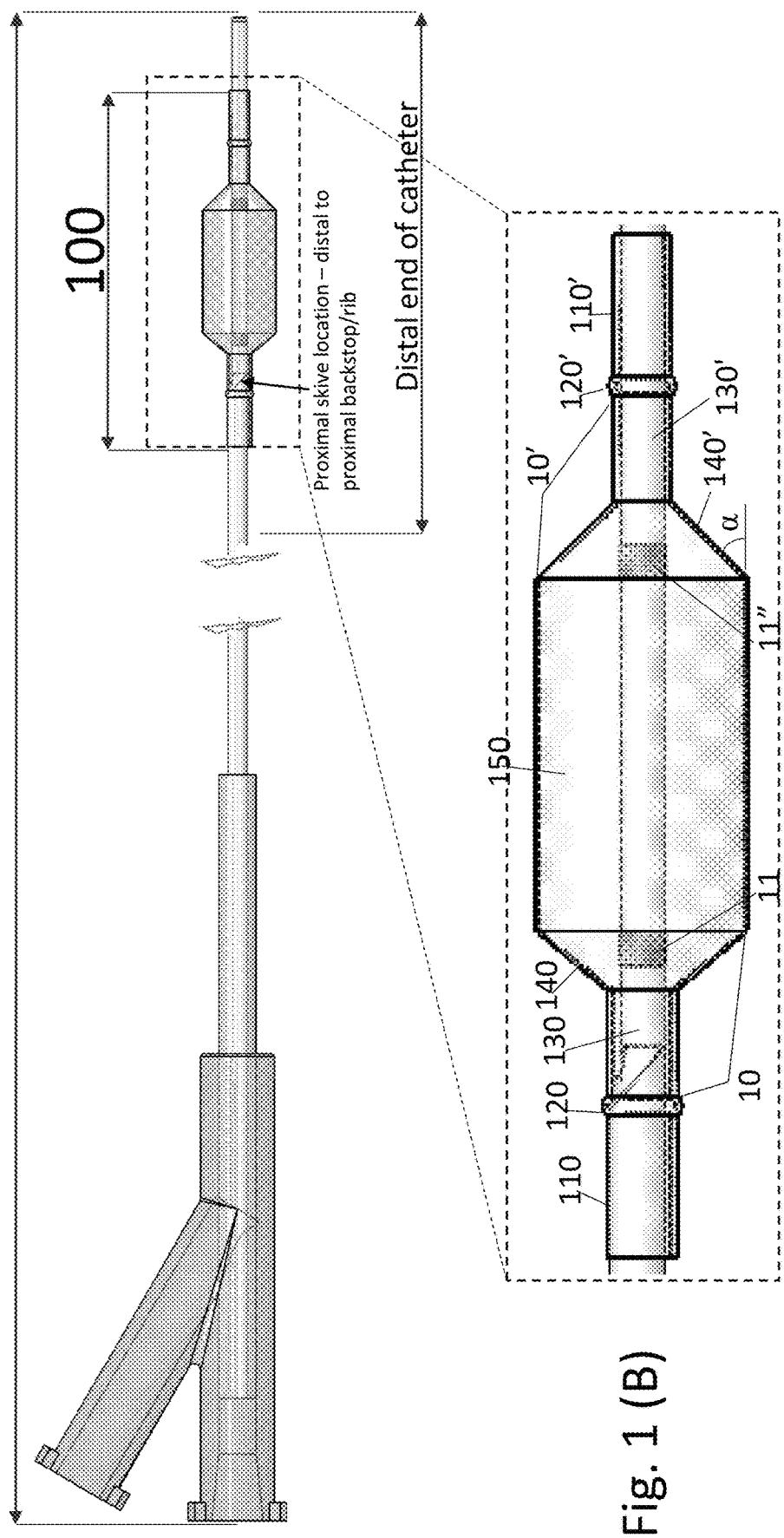
FIG. 1(A) shows a side view of a semi-expanded balloon according to an embodiment of the invention that is mounted to the distal end of a catheter.
FIG. 1(B) shows a close-up view of the balloon at the end of the catheter.

The present application describes embodiments of a balloon which can be made from a single piece of medical balloon tubing which, upon being mounted to a delivery mechanism such as a catheter, can safely and reliably advance, deploy, and post-expand a balloon-expandable/balloon-actuated device such as a stent/BVS with the aid of cuffs. In various embodiments, the balloon and retractable cuffs are part of a balloon system that is designed to safely and effectively deliver a stent, scaffold, and any other medical device that is balloon expandable/actuated.

The present invention provides improvements over existing technology not only because the balloon is specifically designed with features that incorporate cuffs directly into the design, which helps with stent retention, but also because the balloon-cuff combination improves the accuracy of deploying a stent once the implantation site is reached.

One such improvement over previous designs is the ability to re-use the inventive balloon for post-expansion, i.e. re-using the same balloon to re-expand an implanted device following initial placement, without having to swap out balloons following implantation. This feature is particularly useful when implanting balloon-expandable/balloon-actuated devices made from bioabsorbable materials, since these devices are not visible under conventional x-ray technology.

The ability to re-expand delivery balloons, particularly those used for delivering devices such as stents that are made from bioabsorbable materials, can drastically reduce the risk of post-implantation dislodgment and a geographic "miss." Either of these problems with stent placement may arise as a result of device under-expansion and can occur during retrieval/retraction of the delivery system or while traversing an under-expanded device with another device, such as a guide-wire and post-dilatation balloon, during the process of swapping out balloons.

Thus, in various embodiments the presently-disclosed balloon cuff technology provides one or more advantages. In some embodiments, the inventive balloon may include one or two cuffs (sometimes referred to as retractable retention cuffs (RRCs)) directly mounted to the balloon which not only allows for precise stent/scaffold deployment but which also permits re-use of the expanded balloon for post-inflation (e.g. re-inflation/expansion following initial placement of a device such as a stent) without having to switch out an initial delivery balloon for a post-dilatation balloon.

Furthermore, the present balloon makes it possible to perform post-placement expansion because the cuffs retract into receiving trenches or wells. Retraction of the cuffs is a feature designed into the balloon which facilitates containment of the retracted cuffs once the cuffs have retreated down the cones of the balloon, freeing and exposing the balloon's cones and making the entire working length of the balloon available to be re-used for post-placement dilatation.

In certain embodiments the inventive balloon-cuff combination can be mounted and affixed to a catheter, extrusion, and/or other structure having an inflation port, and can be adapted for any balloon-expandable and/or balloon-actuated device.

The inventive balloon-cuff combination is distinguishable by features such as its shapeable backstops, receiving trenches/wells, and/or high-angled balloon cone slopes. When such balloons are combined with retractable retention bands/cuffs, the combination provides a balloon system which allows for the precise expansion and placement of a stent, scaffold, or other device in the body.

As noted herein, some existing stent delivery catheters include specialized bands/sleeves with distinct properties that are optimized to serve a single purpose but which, as a result, need to be changed out in the middle of a procedure, between initial placement of a device and subsequent adjustments or corrections to the placed device.

For example, certain known stent delivery catheters utilize noncompliant balloons which help to create a specific shape, e.g. a cylinder having a defined diameter, when the balloon is inflated. The use of a noncompliant material (i.e. a material that has relatively low elasticity, for example which increases only 4-6% in diameter beyond its nominal dimensions at elevated pressure) allows the use of relatively high pressures to inflate the balloon. A downside of such balloons when placing a stent is that the conventional stent delivery balloon may not be able to conform to a tissue having an uneven shape, with a result that the stent may not be properly seated into a tissue such as a vessel. In some cases, to address this issue the noncompliant balloon that is used for initial stent placement may be deflated and removed and replaced with a more compliant balloon to perform additional adjustments. As a result, two different balloons may be needed: a first balloon may be used to place a stent or other device and then a second balloon may be used to make adjustments or corrections to a stent or other device following initial placement.

One reason that balloons made of compliant materials may not be used for initial placement of a stent is that a compliant balloon may not be capable of creating a particular desired shape (e.g. a cylinder), as the compliant balloon may not be able to press against and reshape obstructions such as tissue (e.g. a constriction in a blood vessel) or the stent and instead may bulge out in areas where there are no opposing forces, such at the ends of the balloon. The failure of a compliant balloon to generate uniformly-applied forces may generate may lead to stents or other devices being improperly seated or in some cases even being damaged.

Accordingly, one solution disclosed herein to the drawbacks associated with using a compliant balloon material is to add cuffs at the ends of the balloon to constrain the inflation of the balloon. As noted above, a stent delivered on a balloon made of a compliant material may fill unevenly due to unequal forces applied to the surface of the balloon, for example by the stent and/or surrounding tissue. As disclosed herein, the addition of cuffs helps to control and direct inflation of the balloon so that the centrally-located working area (around which the stent is generally positioned) fills evenly (e.g. into a cylindrical shape), thereby providing even and controlled expansion of the stent.

In certain embodiments, upon inflation of the balloon the cuffs may retract from the conical ends of the balloon due to one or both of the angles of the cones and the use of a relatively soft material for the cuffs. While the cuffed balloon behaves more like a noncompliant balloon during initial placement of the device, retraction of the cuffs then permits the balloon to behave more like a compliant balloon during subsequent adjustments to the placed device. In addition, the retraction of the cuffs exposes a greater length of the balloon surface, which increases the working area of the balloon that can be used to make adjustments and corrections to the stent following initial placement.

In some embodiments, one or both ends of the balloon may include a "backstop," e.g. a raised portion set at a distance from the central portion of the balloon with a trench in between the backstop and the conical balloon end(s). The backstop helps to stabilize the cuffs and, in the case of a backstop at the distal end of the balloon (away from the catheter), can keep the cuff and stent from dislodging from the balloon assembly. The backstops may have a number of cross-sectional shapes, for example rounded, slanted, or straight, or combinations of these shapes. In a particular embodiment the backstop may be slanted on a side facing away from the balloon cone and may form a flat wall on the side that faces the balloon cone. For a balloon that has two backstops, the backstops do not have to be the same size or shape (e.g. the distal backstop may have a larger diameter to help retain the cuff and/or stent). In certain embodiments, the backstops may increase in diameter and/or become more rigid upon inflation of the balloon, which helps keep the cuffs from sliding too far along the balloon. The backstops help to define a trench area which is between each backstop and the adjacent balloon cone.

When the balloon is inflated, the cuffs are initially associated with the conical ends of the balloon (i.e. the cones), however in certain embodiments the cuffs retract from the cones so that by the time the balloon is inflated the cuffs have retracted to the trench regions, generally with the cuffs abutting the backstops. The cuffs may move off the cones due to one or both of the cuffs sliding along the balloon and the cuff material folding, rolling, or bunching up; in some cases the cuffs abutting the backstops may cause the cuffs to fold, roll, or bunch up, which may affect retraction of the cuffs (e.g. make it proceed more quickly).

The balloon cones may be approximately cone-shaped or may be slightly rounded such that the angle of the cone increases further from the balloon center. The retractability of the cuffs arises in part from the use of a soft and flexible material to make the cuffs (discussed further below) and/or from the balloon cone angle (discussed further below) relative to the long axis of the balloon.

The balloon is formed ahead of time so that it has a central portion on which the stent or other device will be mounted, with cones being formed at each end of the central portion and backstops with intervening trenches on one or both sides of the balloon. In some embodiments, the trench regions on either side of the balloon may have different diameters, for example a larger diameter on the proximal side that engages with a larger portion of the catheter and a smaller diameter on the distal side which may only engage with the guidewire lumen portion of the catheter. The dimensions of the balloon are based on the particular application, for example the type of vessel and the stent that is to be deployed. The central portion of the balloon in particular has a length that is matched to the length of the stent in its compressed state prior to expansion and deployment.

After shaping, the balloon may be "pre-conditioned," meaning it may be pre-inflated (e.g. with air) but with no stent attached and then stretched past its initial inflation point. This pre-conditioning of the balloon helps balloon (re)expansion, particularly in the central portion, during stent deployment.

Once a balloon has been shaped and optionally pre-conditioned, it is folded and pleated and assembled on a catheter. The shaped balloon is slid onto the end of a catheter, which includes a central guidewire lumen or conduit which is paralleled by and disposed within a conduit that terminates at the location where the balloon is mounted to the distal end of the catheter for delivery of inflation fluid to the balloon. The inflation conduit or lumen of the catheter may terminate in an angled aperture created via skiving (where the aperture created this way may be referred to as a "skive"; see FIG. 1(B)). Although the balloon system may be used with any of a number of catheters, in certain embodiments the balloon may be used with either a rapid-exchange catheter or an over-the-wire catheter and may be compatible with guide wires ranging from 0.014" to 0.035".

The outer diameter (OD) of the distal guidewire lumen may include one or more radiopaque marker bands, positioned directly beneath the balloon (e.g. FIG. 9), which may delineate the margins of the "working length" of the balloon, stent, and/or both, for example, during positioning of the stent in the body. This is particularly helpful with stents that are made from materials that are not radiopaque themselves, as is generally the case for bioabsorbable stents. The marker bands may be spaced from one another such that the distance between their inner edges corresponds to the length of the central portion of the balloon. This distance is also approximately the length of the stent that is used with the balloon, that is, the length of the central portion of the balloon, the length of the stent, and the spacing of the marker bands may all be approximately the same, which helps with placement and adjustment via secondary inflation of the stent since the person placing the stent can used the balloon's markers to re-align the stent between the marker bands of the balloon during the adjustment phase. In various embodiments, other numbers and placements of marker bands are also possible.

The proximal end of the balloon is slid over the end of the larger-diameter shaft containing both the guiding and inflation conduits, where the relative positioning of the skived aperture and the proximal backstop (assuming there is a proximal backstop) may determine how quickly the backstop fills with fluid during inflation of the balloon, with a greater degree of overlap between the backstop and the skived aperture promoting a more rapid filling of the backstop.

Once the cuffs are placed on the balloon, a stent or other device can be positioned over the central portion of the balloon and crimped into place. The cuffs are placed so that one end of each cuff completely overlaps (or covers) the marker band (FIG. 6(A)) and the other end extends to the back stop, such that the each cuff covers the cone portion of one end of the balloon as well as the adjacent trench portion. In general, the outer diameters (ODs) of the backstops, the crimped stent, and the placed cuffs are approximately the same so that the balloon assembly has a fairly uniform profile, which helps when inserting the assembly through into the body and as it is maneuvered through a vessel to keep the stent from being dislodged. The cuffs are not needed for holding the stent in place and as a result there may be a gap between the crimped stent and the cuffs.

FIGS. 1(A) and 1(B) show an example of the inventive balloon 100 mounted to the distal end (shown in FIG. 1(B)) of a catheter shown in FIG. 1(A). In some embodiments the balloon 100 may be formed from a medical balloon that is produced in a single step to yield the inventive delivery balloon having one or more distinguishable features, as described in detail below.

FIG. 1(B) shows a close up view of the balloon 100 mounted on a catheter with a pair of cuffs 10, 10' attached thereto. The catheter shaft comprises at least one conduit for delivering inflation fluid to the balloon and may enclose a parallel conduit that runs the partial or entire length to the inflation conduit for the insertion of a guidewire. The inflation conduit terminates in an angled opening created via skiving. The inflation fluid is emitted from the catheter's inflation conduit/lumen into the balloon 100 from the aperture created at the termination of the inflation lumen within the mounted balloon between the outer, proximal portion of balloon 100 and the guidewire lumen. Thus the balloon 100 must fit completely over the inflation conduit at the proximal portion of the catheter in order to ensure that inflation fluid is directed into the balloon 100. In various embodiments, the inflation fluid used may be an iodine-based saline solution/mixture. In certain embodiments, the balloon 100 may be inflated to a pressure in a range of 5 bar to 28 bar. In one particular embodiment, cuffs 10, 10' begin to retract from the cones 140, 140' once the balloon 100 reaches 2 bars of pressure.

Accordingly, the balloon 100 includes a proximal end 110 which fits over the larger diameter proximal portion of the catheter. The balloon 100 further includes a distal end 110' which is sized to fit over the smaller-diameter guidewire lumen at the distal end of the catheter. The balloon 100 in FIG. 1(B) also includes backstops 120, 120' at the proximal and distal ends, respectively. The balloon 100 includes a central portion 150 on which the device (e.g. stent) is mounted to the balloon 100 prior to inflation. The central portion 150 of the balloon 100 has cones 140, 140' at the respective proximal and distal ends thereof. Between each pair of backstops 120, 120' and cones 140, 140' are respective proximal and distal receiving trenches 130, 130'.

Also depicted in FIG. 1(B) are cuffs 10, 10' at the respective proximal and distal ends of the balloon 100. As the balloon 100 is in a semi-expanded state the cuffs 10, 10' have not retracted and are depicted as extending over the cones 140, 140' and the receiving trenches 130, 130'.

In various embodiments, the guidewire lumen may have attached thereto are a pair of radiopaque marker bands 11, 11' (which may be made of materials such as platinum, gold, tantalum, and/or other radiopaque compounds) at respective proximal and distal locations of the guidewire lumen. The marker bands 11, 11' help facilitate both the initial placement of a device as well as the subsequent adjustments and corrections to the device that might need to be made. As shown in FIG. 1(B), in some embodiments the marker bands 11, 11' may be spaced apart so that they overlap with the cones 140, 140', which means that the stent or other device that is loaded onto the central portion 150 of the balloon 100 is located between the marker bands 11, 11'. In addition, following initial placement of the device, a user such as a clinician will know that the central portion 150 of the balloon 100 is located between the marker bands 11, 11', which facilitates placement of the balloon 100 for subsequent adjustments and corrections. While the use of radiopaque marker bands 11, 11' is useful for placement of any device, it is particularly helpful for placement of biodegradable stents in which the stent material is not detectable with conventional x-ray based imaging techniques.

In particular embodiments, the balloon 100 may be made from a low compliance material, such as nylon, to allow for high pressure inflation and overexpansion i.e., at ≥10% above the balloon's nominal pressure. Nevertheless, in various embodiments the balloon may be made from other known materials used to make medical balloons, including without limitation: nylon elastomers, polyethylene terephthalate, polyether block amide (PEBA), and urethanes.

Figure 2:
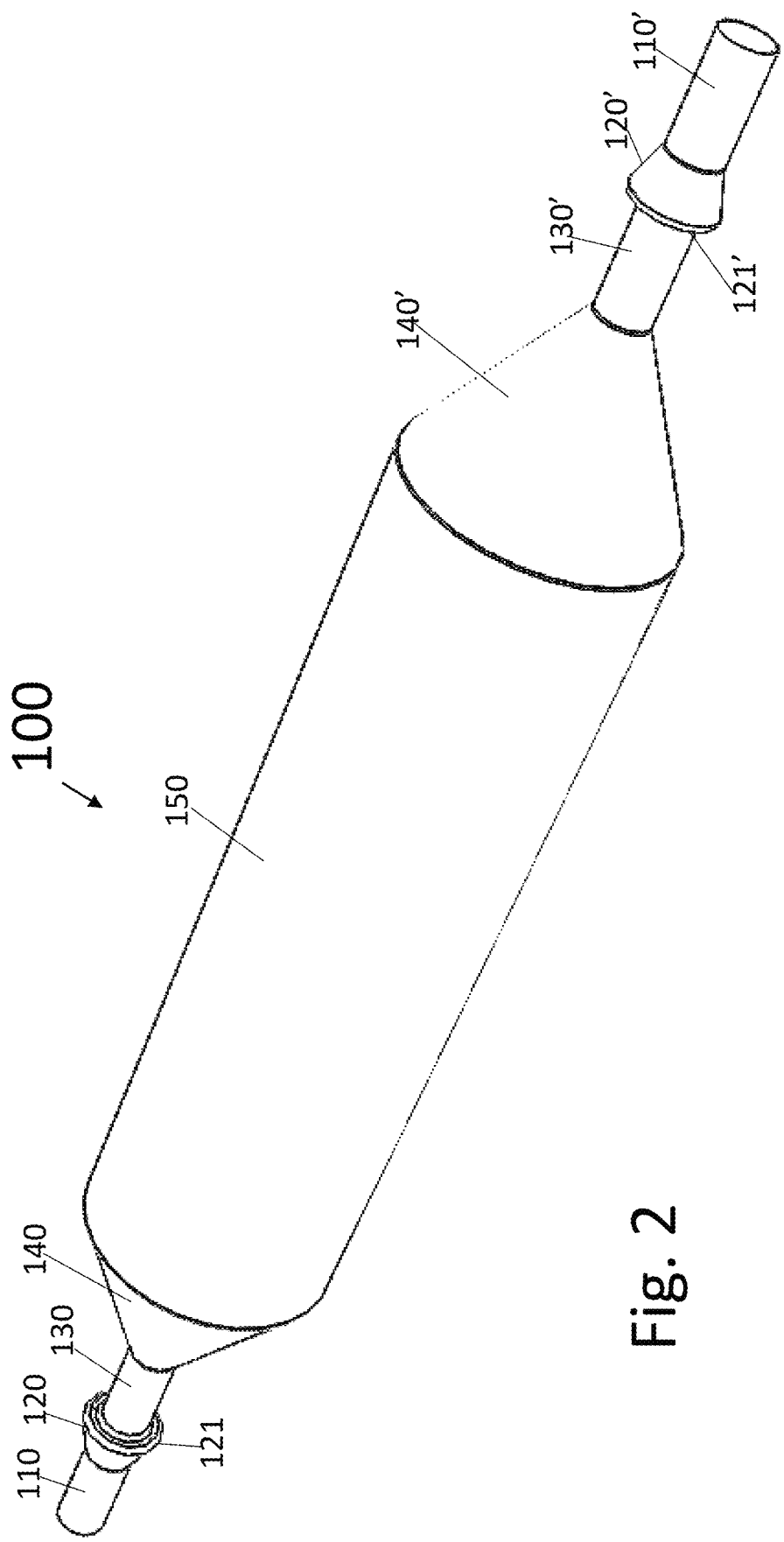
FIG. 2 shows a perspective view of a balloon according to an embodiment of the invention.

FIG. 2 shows a delivery balloon 100 by itself, following initial formation and before being mounted onto a catheter or having a stent or cuffs added. The balloon 100 of FIG. 2 includes the central portion or working area 150 with the cones 140, 140' at the ends along with two backstops 120, 120' (for example having backstops that may be either tapered or rounded), receiving trenches or wells 130, 130', where silicone-based bands/cuffs may be loaded into place as a final step of a balloon assembly process and which may also serve as retention cuff receptacles once the cuffs are fully retracted down the balloon cones. In various embodiments the proximal and distal balloon cones 140, 140' may have a minimum slope angle of 30° but less than 90°. In some embodiments, one or both of the backstops 120, 120' may include a relatively straight wall portion 121, 121' facing the balloon cones 140, 140' and perpendicular to the surface of the trench or well 130, 130', to provide a surface against which the cuffs may be pressed during inflation of the balloon and deployment of a stent (FIG. 2). As discussed below, the "height" of the wall portions 121, 121' (that is, the distance from the surface of the trench or well 130, 130' to the outer edge of the respective wall portion 121, 121') may help determine the wall thickness of a cuff that can be used in conjunction with a particular balloon.

In certain other embodiments, the slope angle "α" (see FIG. 1(B)) of the balloon cones 140, 140', measured from the base of the receiving trenches/wells 130 to the working area 150 of the balloon in its fully-expanded state, may be between 50°-70°; in embodiments in which the cones 140, 140' are rounded (see FIGS. 4(A), 4(B)) the slope angle is evaluated at a point approximately midway between the end of the central portion 150 and the neck where the cones 140, 140' meet the respective receiving trenches 130, 130'. The higher-angled balloon cones facilitate the retraction of cuffs (illustrated in FIG. 3) down the slope of the cones as the balloon is inflated. The higher cone-slope angles also allow for "squaring" of the balloon, which provides for more precise and uniform expansion. As used herein, "squaring" of the balloon refers to producing relatively uniform expansion of the balloon, particularly in the central working area 150. For example, the central portion 150 in various embodiments is approximately cylindrical and thus squaring of the balloon during inflation refers to the central portion 150 substantially achieving its cylindrical form.

This squaring effect is aided by the elastic tension of the cuffs 10, 10' compressing against the balloon's cones 140, 140' and receiving trenches or wells 130, 130', allowing the non-cuffed/non-banded working area 150 of the balloon 100 to fill first and by promoting backfilling of the backstops 120, 120' as the diameter of the balloon 100 increases during pressurization. This causes the cuffs 10, 10' to begin to be compressed longitudinally as fluid fills both the balloon 100 and backstops 120, 120', creating a counter-pressure that forces the cones 140, 140' into achieving and maintaining the higher angles throughout balloon pressurization (FIGS. 4(A) and 4(B)).

FIGS. 3(A)-3(C) show the positions of the cuffs 10, 10' at various stages of inflation of a balloon 100. The cuffs 10, 10' are shown to be completely overlapping with the receiving trenches 130, 130' and the cones 140, 140' prior to inflation in the folded state (FIG. 3(A)) and in an early stage of inflation in a semi-expanded state (FIG. 3(B)) but are retracted from the cones 140, 140' and disposed substantially within the receiving trenches 130, 130' in the fully-expanded state (FIG. 3(C)). As can be seen by comparing FIGS. 3(A) and 3(B) to FIG. 3(C), during retraction the cuffs 10, 10' abut the backstops 120, 120' and fold and/or bunch up within the receiving trenches 130, 130'. Although the cuffs 10, 10' are shown as completely covering the cones 140, 140' prior to inflation in the embodiment of FIG. 3(A), in various other embodiments the cuffs 10, 10' may only partially cover the cones 140, 140' (e.g. may only cover 75% of the cones) prior to inflation. In various embodiments, the cuffs may cover between 50% and 100% of the area of the cones 140, 140' prior to inflation of the balloon 100.

In some embodiments, the balloon 100 may have a "shorter" overall length relative to the working length, for example having a working length that is no more than about 2 mm greater than the length of the mounted stent. Combined with the higher-angled cone slopes and the retractable cuffs, which constrain the cones during the initial phase of balloon pressurization, the "shorter" overall balloon length better correlates with the length of the stent and helps ensure less protrusion of the balloon outside the edges of the stent during stent deployment. This minimizes the risk of balloon-induced injury during stent deployment and gives the balloon more of a "squared" shape during inflation and contributes to a more uniform expansion of the stent or other device.

In various embodiments, the shape and size of the backstops 120, 120' as well as the profile (e.g. which may be expressed in "French" units) of the backstops and cuffs in relation to the stent that is mounted to the balloon may be a function of factors such as: the type of stent that the balloon will be used with; the anatomy of the device implantation site; the characteristics of the tissue to be navigated; and whether the device is being used for direct, primary, and/or bailout stenting. For example, a stent for placement in a coronary artery may have thinner struts compared to a stent used elsewhere in the body, e.g. in a vein or bile duct, which may have thicker struts. Furthermore, the balloon that is to be used in a coronary artery would have backstops that are conical on one side and flat/square on the other, with a relatively low cone angle (e.g., 30°) on the conical portion of the backstops to accommodate the smaller and possibly tighter cardiac anatomy, and could be used for direct or primary stenting (and with a thinner strut stent). On the other hand, in a larger artery, such as leg artery or vessel in the body, the backstops could be more rounded (e.g. approximately spherical) or squared (e.g. cylindrical with flat sides).

Furthermore, the length and thickness of the cuffs 10, 10', the slope angles of the cones 140, 140', and the positions of the radiopaque marker bands 11, 11' are related to the length and size of the balloon 100 and the device that is to be mounted to it.

In a preferred embodiment, the profile of the backstops 120, 120' can have outer diameters (OD) ranging from 100 to 1000 microns (0.1 to 1 mm). Moreover, the OD of the backstop may or may not correspond to the OD of a crimped stent, for example the OD of the backstop may in some cases be larger than that of the crimped stent and in other cases may be smaller. However, the "height" (i.e. how far the backstop projects outward beyond the receiving trench, which is related to its OD) of the backstops will determine the wall thickness of the retractable cuffs, which in various embodiments may range from ¼ to ¾ of the height of the backstop. FIG. 5 depicts the height of backstop 120 relative to the height of silicone cuff 10; the cuff 10 abuts the backstop 120 but a rounded portion of the backstop 120 extends further outward than the cuff 10 in this example. In some embodiments, a larger diameter balloon may require retractable cuffs with a greater wall thickness to ensure that the balloon cones are constrained during the initial phases of balloon inflation, ensuring the "squaring off" of the balloon during stent expansion.

In certain embodiments the retractable retention cuff 10 may be made from a material that is or includes a low durometer silicone ranging in Shore durometer of 40A-50A (e.g. in the "Extra Soft" to "Soft" range on the Shore scale). The use of a low durometer Shore A tubing provides a softer material for the cuffs, which permits the cuffs to retract more easily once the balloon reaches its nominal pressure. In various embodiments, the ID of the silicone tubing used for cuff 10 may be less than or equal to the OD of the balloon's receiving trenches/wells 130, 130' after the balloon has been mounted to the catheter, where the OD of the balloon's receiving wells 130, 130' (see, e.g. FIG. 1(B), 5) depend on the wall thickness of the medical balloon extrusion used to make the balloon. For example, in one embodiment, the OD of the balloon's receiving wells may add 0.014"-0.018" to the overall profile of the distal end of the catheter once the balloon is mounted. Given that the proximal and distal receiving wells 130, 130' may have different outer diameters (see FIG. 1(B)) the proximal and distal cuffs 10, 10' may be extruded to have corresponding inner diameters that are suitably different sizes.

Figure 6A:
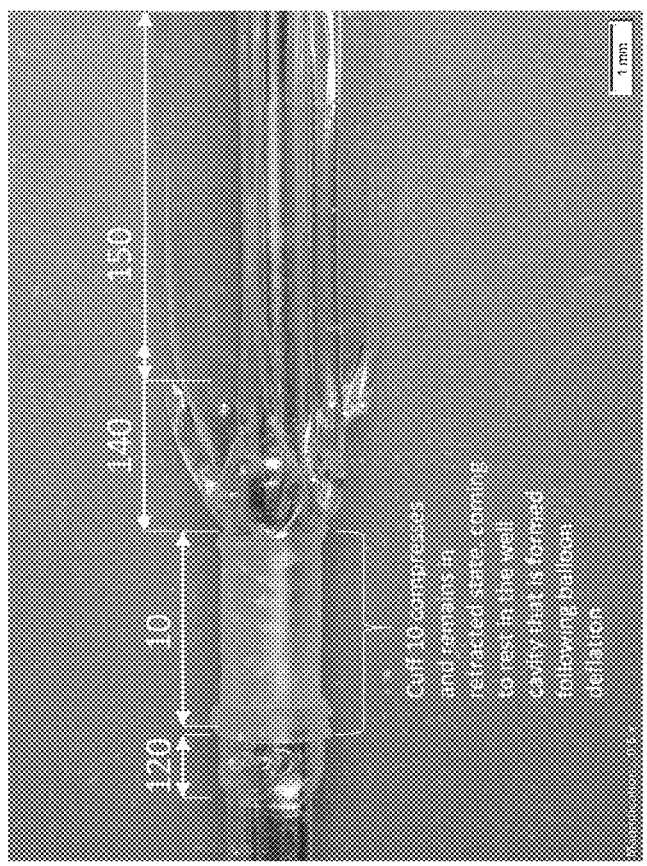
FIGS. 6(A) and 6(B) show the position of a cuff on an embodiment of a balloon before (FIG. 6(A)) and after (FIG. 6(B)) inflation.

In contrast to certain known systems in which bands or sleeves may be adhered (e.g. using adhesive) to the balloon and/or the catheter, the cuffs 10, 10' of the present device are held in place by elastic tension to the cones 140, 140' at either end of the balloon and in the receiving trenches or wells 130, 130'. FIG. 6(A) is a representative image of a proximally-mounted cuff 10 loaded on balloon 100 between backstop 120 and marker band 11 placed into the balloon's receiving trench/well 130.

The length of cuff 10 (FIG. 6(A)) can vary from balloon to balloon, but is generally based on the distance between the backstops 120, 120'/backstop walls 121, 121' and the position of the marker bands 11 on the balloon 100. When the cuffs 10, 10' are added to the balloon in a final assembly step, the balloon may be in a pleated and folded state. In one embodiment, the balloon has at least four pleats. However, in other embodiments the balloon may have less than or greater than four pleats.

Although the ID of the cuffs 10, 10' (e.g. which may be made of silicone) is important for retention of the cuffs 10, 10' on the balloon, the cuff wall thickness may also be a factor. In particular, maintaining cuff wall-thickness uniformity while the cuffs are slid into place may be important to avoid overstretching and tearing of the cuffs. In various embodiments, ensuring uniformity in wall thickness as the cuffs are slid into position over the balloon may be aided by lubricating the surface of the balloon using a solvent, such as alcohol, to limit friction while sliding the cuffs into place.

Figure 6B:
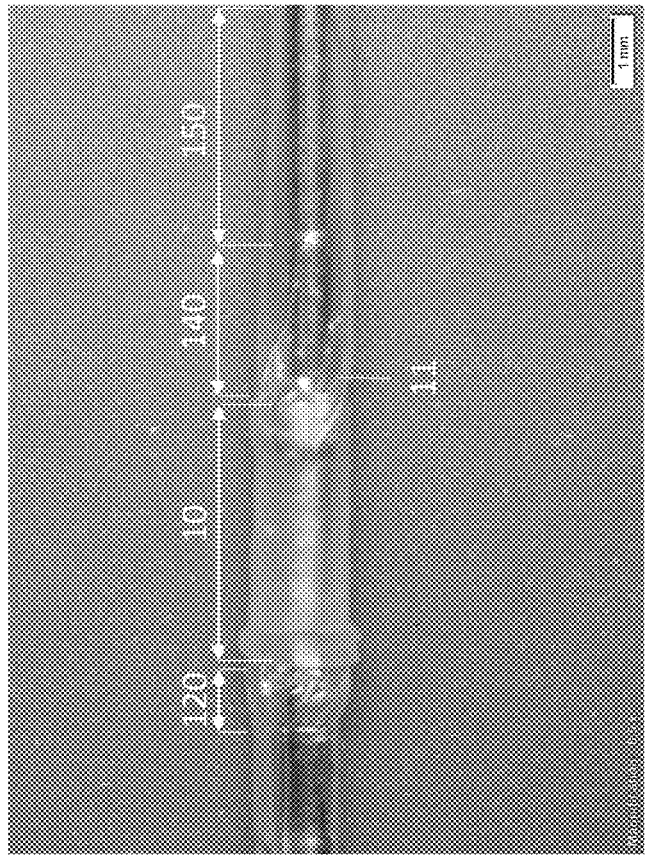

The use of relatively soft low durometer cuff material permits the cuffs to retract during balloon expansion. The high-angled slopes of the balloon cones 140, 140' facilitate the retraction, forcing the cuffs 10, 10' down the slope toward the balloon's receiving wells/trenches 130, 130'. The use of steeper balloon cones 140, 140' combined with pressurized backstops 120, 120' prevent the cuff from coming completely off the balloon (FIG. 4B), allowing the cuffs to come to rest inside the receiving wells or trenches 130 (FIG. 6B) once the balloon is depressurized.

In the present embodiment, the distal backstop 120' or both backstops 120, 120' are pressurized during balloon inflation, aiding in the retraction of the cuffs 10, 10' and preventing the cuff (primarily the distal cuff 10') from coming off the distal end of the catheter. Whether one or both backstops 120, 120' become pressurized during balloon inflation depends on the location of the aperture (skive) on the distal inflation conduit (FIG. 5).

FIG. 5 shows the location of the skive on the distal inflation shaft of the distal end of the catheter immediately distal to the proximal backstop wall 120. The location of the skive relative to its position of the proximal backstop affects the amount of inflation fluid the proximal backstop receives during balloon pressurization. The skive's location relative to the proximal backstop is based on the size and diameter of the balloon, the amount of pressure required to inflate the balloon and to initiate the cuff retraction process, and the Shore durometer and wall thickness of the cuffs.

Figure 7A:
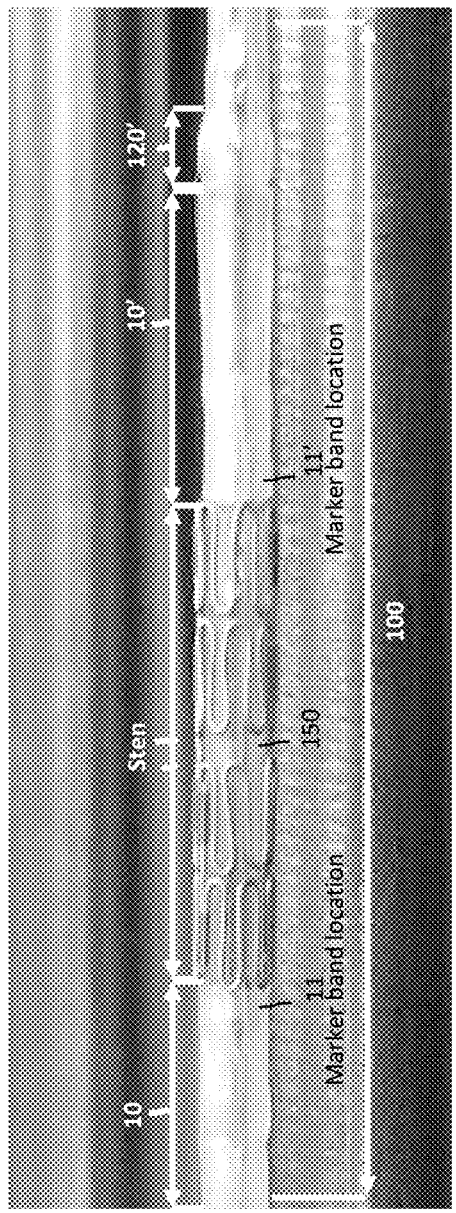
FIGS. 7(A) and 7(B) show embodiments of a balloon in a non-inflated state having a crimped stent and a pair of cuffs thereon.
Figure 7B:
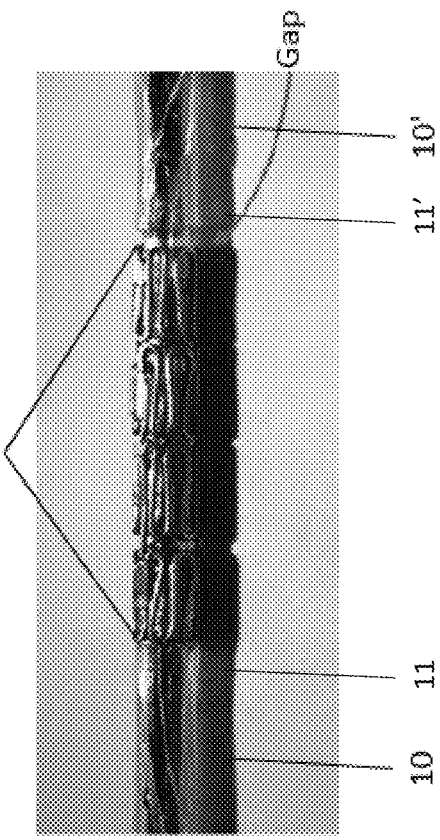
Figures 8A, 8B:
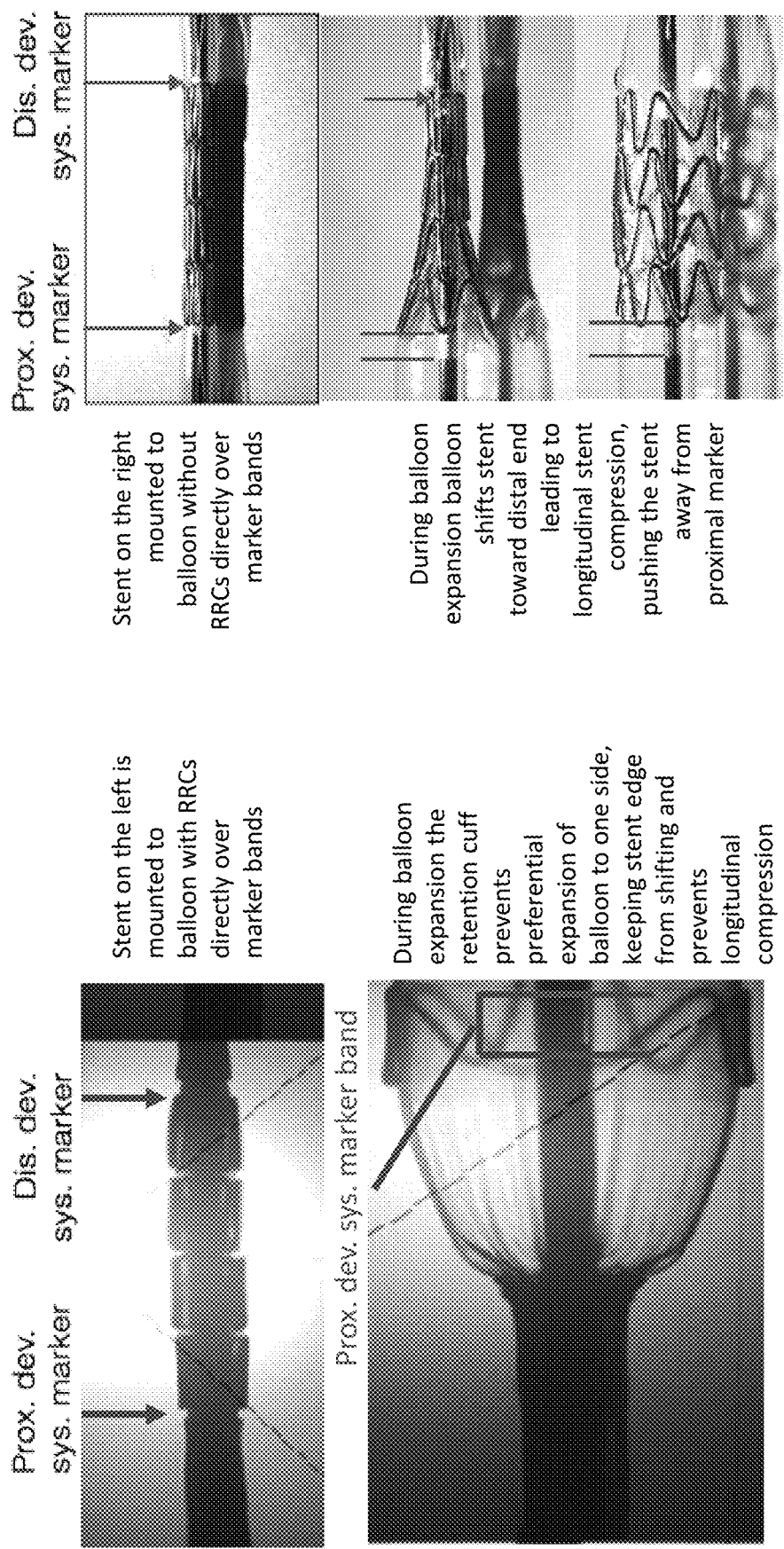
FIGS. 8(A) and 8(B) show embodiments of a balloon system having a stent crimped thereon at various stages of inflation.
Figure 9:
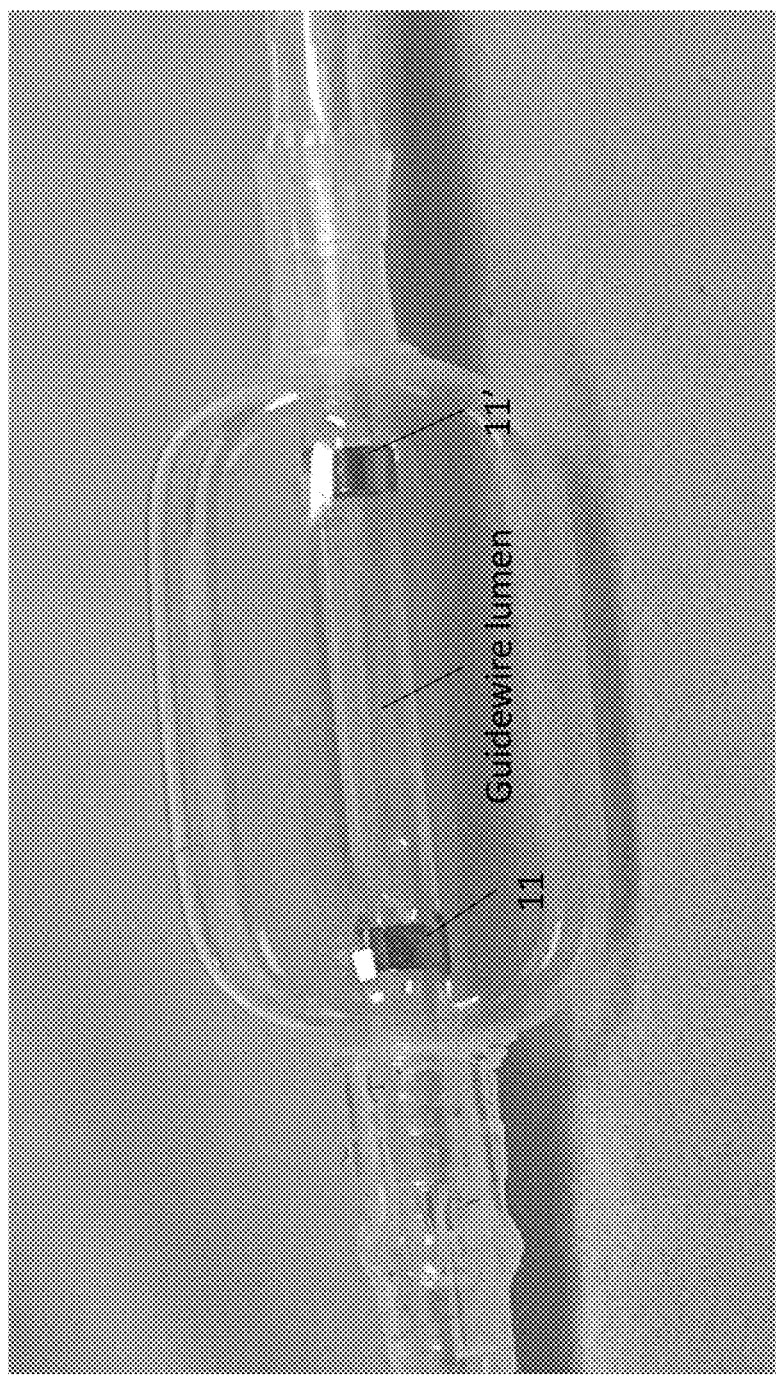
FIG. 9 shows an embodiment of a balloon mounted on a catheter in which the balloon has been inflated without a stent or other device present, showing the locations of the marker bands on the guidewire lumen.

Once a balloon 100 has been shaped and optionally pre-conditioned, it is assembled onto a catheter with cuffs 10, 10' and a device such as a stent. FIGS. 7(A) and 7(B) show examples of a stent crimped onto the balloon system. On either side of the stent are cuffs 10, 10' that have a thickness that is comparable to the thickness of the stent. As noted above, the stent is not held in place by the cuffs 10, 10', and indeed in some cases there may be a gap between the stent and the cuffs 10, 10' as shown in FIG. 7(B). Also as indicated above, the device such as a stent may be disposed over the balloon in a position that is indicated by a pair of marker bands 11, 11'. As shown in the embodiment of FIG. 8(B) the stent may be disposed between the inner edges of the marker bands 11, 11', as indicated by the arrows in the top panel of FIG. 8(B) and the pairs of parallel lines in the middle and lower panels of FIG. 8(B). FIG. 9 shows another embodiment of a balloon mounted on a catheter in which the balloon has been inflated without a stent or other device present so that the marker bands 11, 11' can clearly be seen on the guidewire lumen.

FIGS. 8(A) and 8(B) provide images showing inflation of a balloon with (FIG. 8(A)) and without (FIG. 8(B)) cuffs. FIG. 8(A) shows a balloon having cuffs on each end that goes from being uninflated (FIG. 8(A), top panel) to fully inflated (FIG. 8(A), lower panel), demonstrating the even inflation and expansion of the stent and retraction of the cuff on the left side of the balloon. FIG. 8(B) shows an initially non-inflated balloon without cuffs and having a stent crimped thereon (FIG. 8(B), top panel) being inflated (FIG. 8(B), middle panel) until the central portion forms an approximate cylindrical shape (FIG. 8(B), lower panel). Note that in the absence of cuffs the balloon inflates unevenly, proceeding from left to right, which can cause problems during implantation such as causing a geographic miss and stress on the stent (particularly for stents made of bioabsorbable materials). Note also in FIG. 8 that marker bands can be placed on the guidewire lumen so that they are either outside of the location of the device/stent (FIG. 8(B)) or within the location of the device/stent (FIG. 8(A)).

Figure 10:
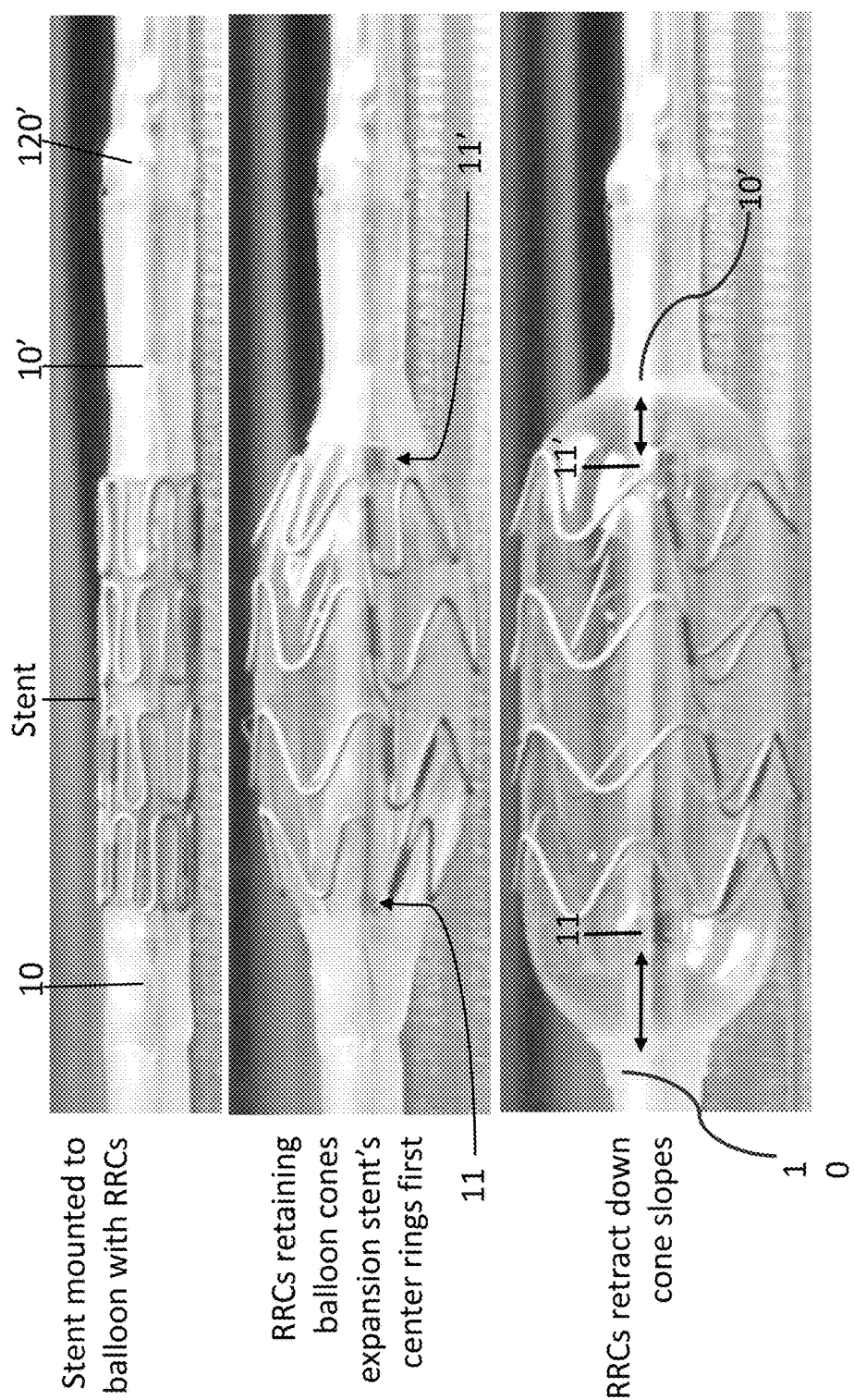
FIGS. 10 and 11 show an embodiment of a balloon system having a stent crimped thereon at various stages of inflation (FIG. 10) and deflation (FIG. 11), from a non-inflated state (FIG. 10, top panel), to an inflated state (FIG. 10, middle and lower panels), to a deflated state (FIG. 11, top panel), to a re-inflated state (FIG. 11 middle panel), and finally to a "re-deflated" state (FIG. 11, lower panel).
Figure 11:
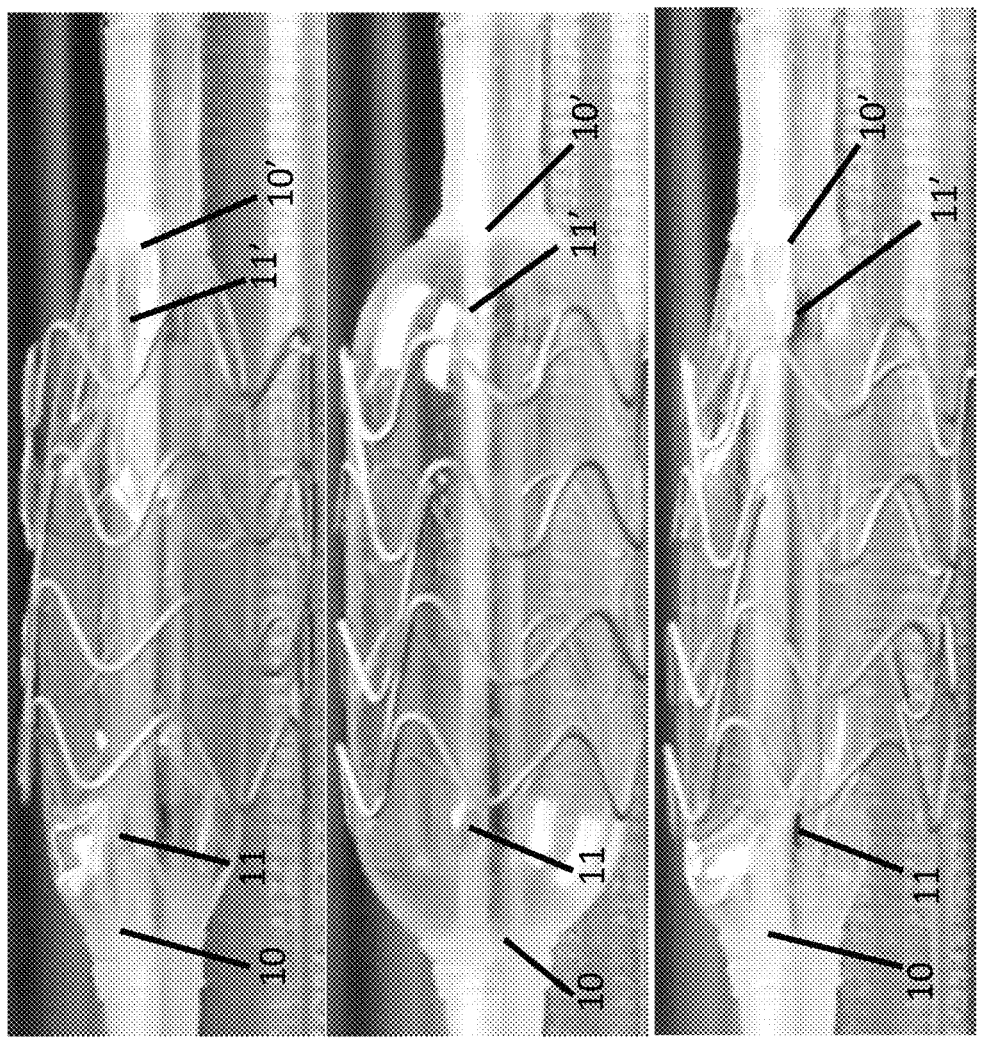

Similarly, FIGS. 10 and 11 show a series of images of one end of an embodiment of a balloon system with cuffs 10, 10' having a stent attached thereto. FIG. 10 shows an initially non-inflated balloon (top panel) being inflated such that the cuffs 10, 10' retract (middle and lower panels) and then the balloon is deflated (FIG. 11, top panel) leaving the expanded stent in place and the cuffs retracted. Given that the cuffs fold and/or bunch up during retraction, the cuffs do not re-cover the cones following deflation of the balloon. As can be seen in FIG. 11 the working length of the balloon is increased by the retraction of the cuff, which facilitates secondary inflations (post-dilatations) to make adjustments (FIG. 11, middle and lower panels) to the implanted stent. In this particular embodiment, the marker bands 11, 11' are located laterally relative to the stent in a non-overlapping location. The embodiment of FIGS. 10 and 11 further demonstrates the utility of the cuffs in retaining the stent's position on the balloon during inflation i.e., not "pushing/displacing" the stent on the balloon during primary inflation of the balloon to expand the mounted stent.

Although the various exemplary embodiments disclosed herein have focused on the placement of stents, particularly biodegradable stents, in various other embodiments the disclosed balloon delivery system can be used to place a variety of types of balloon-expandable stents or stent like scaffolds including those used outside the vasculature, such as in ducts, cavities, appendages throughout the body, as well as other balloon-actuated devices including those made from super-elastic and/or memory-shaped alloys, such as nickel-titanium and biodegradable thermoplastic elastomers, such as caprolactone.

The present invention has been described in terms of one or more preferred versions, and it should be appreciated that many equivalents, alternatives, variations, additions, and modifications, aside from those expressly stated, and apart from combining the different features of the foregoing versions in varying ways, can be made and are within the scope of the invention. The true scope of the invention will be defined by the claims included in any later-filed utility patent application claiming priority from this provisional patent application.

What is claimed is:

1. A balloon system for delivery of a device, comprising:
a balloon comprising:
an elongated central portion including a proximal tapered cone and a distal tapered cone,
the elongated central portion and the proximal and distal tapered cones being in an uninflated state;
a proximal end located proximal to the proximal tapered cone and a distal end located distal to the distal tapered cone,
a proximal backstop located between the proximal end and the proximal tapered cone,
the proximal backstop comprising a proximal raised portion of the balloon,
a distal backstop located between the distal end and the distal tapered cone,
the distal backstop comprising a distal raised portion of the balloon,
a proximal receiving trench defined by the proximal tapered cone and the proximal backstop,
a distal receiving trench defined by the distal tapered cone and the distal backstop, and
a proximal retractable cuff disposed over the proximal receiving trench and the proximal tapered cone and a distal retractable cuff disposed over the distal receiving trench and the distal tapered cone,
wherein, upon inflation of the balloon, the proximal retractable cuff retracts from the proximal tapered cone such that the proximal retractable cuff retreats from the proximal tapered cone and is contained substantially within the proximal receiving trench.

2. The balloon system of claim 1, wherein, upon inflation of the balloon,
the distal retractable cuff retracts from the distal tapered cone such that the distal retractable cuff retreats from the distal tapered cone and is contained substantially within the distal receiving trench.

3. The balloon system of claim 1, wherein, upon inflation of the balloon, at least one of the proximal tapered cone or the distal tapered cone has an angle relative to a long axis of the balloon of at least 30°.

4. The balloon system of claim 1, wherein, prior to inflation of the balloon, the elongated central portion is folded.

5. The balloon system of claim 1, wherein, upon inflation of the balloon, at least one of the proximal backstop or the distal backstop is inflated.

6. The balloon system of claim 1, wherein at least one of the proximal backstop or the distal backstop comprises a wall portion facing the respective proximal tapered cone or distal tapered cone,
wherein the wall portion is perpendicular to the respective proximal receiving trench or distal receiving trench.

7. The balloon system of claim 1, wherein at least one of the proximal retractable cuff or the distal retractable cuff comprises a low durometer silicone material.

8. The balloon system of claim 1, wherein the balloon comprises a low compliance material.

9. The balloon system of claim 8, wherein the low compliance material comprises nylon.

10. The balloon system of claim 1, further comprising a stent in a compressed state surrounding the central portion of the balloon.

11. The balloon system of claim 10, wherein, upon inflation of the balloon, the stent is expanded by the balloon to an expanded state.

12. The balloon system of claim 1, wherein at least one of the proximal raised portion or the distal raised portion comprises a rounded or conical portion of the balloon.

13. A balloon system for delivery of a device, comprising:
a balloon comprising:
an elongated central portion including a first tapered cone at a first, proximal end thereof and a second tapered cone at a second, distal end thereof,
the elongated central portion and the first and second tapered cones being in an uninflated state;
a first end located proximal to the first tapered cone and a second end located distal to the second tapered cone,
a first backstop located between the first end and the first tapered cone,
the first backstop comprising a first raised portion of the balloon,
a second backstop located between the second end and the second tapered cone,
the second backstop comprising a second raised portion of the balloon,
a first receiving trench defined by the first tapered cone and the first backstop,
a second receiving trench defined by the second tapered cone and the second backstop,
a first retractable cuff disposed over the first receiving trench and the first tapered cone and a second retractable cuff disposed over the second receiving trench and the second tapered cone,
upon inflation of the balloon,
the first retractable cuff retracting from the first tapered cone such that the first retractable cuff retreats from the first tapered cone and is contained substantially within the first receiving trench, and
the second retractable cuff retracting from the second tapered cone such that the second retractable cuff retreats from the second tapered cone and is contained substantially within the second receiving trench.

14. The balloon system of claim 13, wherein, upon inflation of the balloon, at least one of the first tapered cone or the second tapered cone has an angle relative to a long axis of the balloon of at least 30°.

15. The balloon system of claim 13, wherein, prior to inflation of the balloon, the elongated central portion is folded.

16. The balloon system of claim 13, wherein, upon inflation of the balloon, at least one of the first backstop or the second backstop is inflated.

17. The balloon system of claim 13, wherein at least one of the first backstop or the second backstop comprises a wall portion facing the respective first tapered cone or second tapered cone,
wherein the wall portion is perpendicular to the respective first receiving trench or second receiving trench.

18. The balloon system of claim 13, wherein at least one of the first retractable cuff or the second retractable cuff comprises a low durometer silicone material.

19. The balloon system of claim 13, wherein the balloon comprises a low compliance material.

20. The balloon system of claim 19, wherein the low compliance material comprises nylon.

21. The balloon system of claim 13, wherein at least one of the first raised portion or the second raised portion comprises a rounded or conical portion of the balloon.

22. A method of placing a device in a vessel, comprising:
inserting a catheter comprising a balloon system into the vessel,
  the balloon system comprising a balloon, a proximal retractable cuff, and a distal retractable cuff,
  the balloon comprising:
    an elongated central portion including a proximal tapered cone and a distal tapered cone,
    the elongated central portion and the proximal and distal tapered cones being in an uninflated state, and
    the device being disposed around the elongated central portion,
    a proximal end located proximal to the proximal tapered cone and a distal end located distal to the distal tapered cone,
    a proximal backstop located between the proximal end and the proximal tapered cone,
      the proximal backstop comprising a proximal raised portion of the balloon,
    a distal backstop located between the distal end and the distal tapered cone,
      the distal backstop comprising a distal raised portion of the balloon,
    a proximal receiving trench defined by the proximal tapered cone and the proximal backstop,
    a distal receiving trench defined by the distal tapered cone and the distal backstop, and
  the proximal retractable cuff being disposed over the proximal receiving trench and the proximal tapered cone and the distal retractable cuff being disposed over the distal receiving trench and the distal tapered cone;
inflating the balloon with inflation fluid to expand the elongated central portion of the balloon,
  the device being expanded in cross-sectional size upon inflation of the balloon, and
  upon inflation of the balloon, the proximal retractable cuff being retracted from the proximal tapered cone such that the proximal retractable cuff retreats from the proximal tapered cone and is contained substantially within the proximal receiving trench, and the distal retractable cuff being retracted from the distal tapered cone such that the distal retractable cuff retreats from the distal tapered cone and is contained substantially within the distal receiving trench; and
deflating the balloon by removing at least a portion of the inflation fluid.

23. The method of claim 22, further comprising:
re-inflating the balloon with inflation fluid to further expand at least a portion of the device.

24. The method of claim 22, wherein the device comprises a stent.

25. The method of claim 22, wherein inflating the balloon with inflation fluid further comprises:
inflating the balloon with inflation fluid until at least one of the proximal tapered cone or the distal tapered cone has an angle relative to a long axis of the balloon of at least 30°.

26. The method of claim 22, wherein, prior to inflation of the balloon, the elongated central portion is folded.

27. The method of claim 22, wherein inflating the balloon with inflation fluid further comprises:
inflating the balloon with inflation fluid until at least one of the proximal backstop or the distal backstop is inflated with inflation fluid.

28. The method of claim 22, wherein at least one of the proximal backstop or the distal backstop comprises a wall portion facing the respective proximal tapered cone or distal tapered cone, wherein the wall portion is perpendicular to the respective proximal receiving trench or distal receiving trench.

29. The method of claim 22, wherein at least one of the proximal retractable cuff or the distal retractable cuff comprises a low durometer silicone material.

30. The method of claim 22, wherein the balloon comprises a low compliance material.

31. The method of claim 30, wherein the low compliance material comprises nylon.

32. The balloon system of claim 22, wherein at least one of the proximal raised portion or the distal raised portion comprises a rounded or conical portion of the balloon.

* * * * *